United States Patent
Custer et al.

(10) Patent No.: US 10,463,596 B1
(45) Date of Patent: Nov. 5, 2019

(54) SCALP CARE COMPOSITION WITH WELL DISPERSED PARTICULATE SCALP BENEFIT AGENTS

(71) Applicant: The Procter & Gamble Company, Cincinnati, OH (US)

(72) Inventors: Daniel Lawrence Custer, West Chester, OH (US); Elizabeth Rebecca Aistrup, Cincinnati, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

(21) Appl. No.: 16/021,842

(22) Filed: Jun. 28, 2018

(51) Int. Cl.
  *A61K 8/81* (2006.01)
  *A61Q 5/00* (2006.01)
  *A61K 8/58* (2006.01)

(52) U.S. Cl.
  CPC .............. *A61K 8/8147* (2013.01); *A61K 8/58* (2013.01); *A61Q 5/006* (2013.01)

(58) Field of Classification Search
  None
  See application file for complete search history.

(56) References Cited

U.S. PATENT DOCUMENTS

| | | |
|---|---|---|
| 4,329,334 A | 5/1982 | Su et al. |
| 4,867,971 A | 9/1989 | Ryan et al. |
| 6,284,234 B1 | 9/2001 | Niemiec et al. |
| 6,908,912 B2 | 6/2005 | Rioux et al. |
| 7,001,594 B1 | 2/2006 | Peffly et al. |
| 7,026,308 B1 | 4/2006 | Gavin et al. |
| 7,455,851 B1 | 11/2008 | Nelson et al. |
| 7,674,785 B2 | 3/2010 | Gavin et al. |
| 8,206,732 B2 | 6/2012 | Nelson et al. |
| 8,313,782 B2 | 11/2012 | Guthery |
| D681,876 S | 5/2013 | Murdock et al. |
| D690,876 S | 10/2013 | Murdock et al. |
| 8,679,552 B2 | 3/2014 | Guthery |
| 8,796,252 B2 | 8/2014 | Rioux et al. |
| 8,858,968 B2 | 10/2014 | Potin |
| 9,456,969 B2 * | 10/2016 | Aistrup .................. A61Q 5/006 |
| 9,549,885 B2 | 1/2017 | Aistrup |
| 2003/0008855 A1 | 1/2003 | Simon et al. |
| 2003/0157088 A1 | 8/2003 | Elliott et al. |
| 2003/0180242 A1 | 9/2003 | Eccard et al. |
| 2009/0264449 A1 | 10/2009 | Iwata et al. |
| 2011/0268684 A1 | 11/2011 | Battermann et al. |
| 2012/0103151 A1 | 5/2012 | Jones et al. |
| 2012/0134948 A1 | 5/2012 | Springer et al. |
| 2012/0251627 A1 | 10/2012 | Nelson et al. |
| 2013/0115315 A1 | 5/2013 | Derkx |
| 2013/0284195 A1 | 10/2013 | Murdock et al. |
| 2014/0349902 A1 | 11/2014 | Allef et al. |
| 2015/0065476 A1 | 3/2015 | Aistrup et al. |
| 2015/0306006 A1 | 10/2015 | Aistrup et al. |
| 2015/0349902 A1 | 12/2015 | Moulsley et al. |

FOREIGN PATENT DOCUMENTS

| | | | |
|---|---|---|---|
| EP | 0639368 A1 | 2/1995 | |
| EP | 0914816 A1 | 5/1999 | |
| FR | 2976801 B1 | 7/2013 | |
| JP | 2005206538 | 8/2005 | |
| KR | 2002012356 A * | 2/2002 | .............. A61K 7/06 |
| WO | WO2007010478 A2 | 1/2007 | |
| WO | WO2010018418 A1 | 2/2010 | |
| WO | WO2013050241 A1 | 4/2013 | |

OTHER PUBLICATIONS

Machine translation of KR 2002012356 A, dated Feb. 16, 2002 (retrieved by STIC on Mar. 25, 2019).*
"2-in-1 anti-dandruff & styling gel", Mintel GNPD, Schwarzkopf & DEP, Nov. 2004.
"Gel", Mintel GNPD, Davines, Apr. 2012.
"Soothing Serum", Mintel GNPD, Nioxin Research Laboratories, Feb. 2009.
All final and non-final office actions for U.S. Appl. No. 14/478,305 (P&G Case 13046).
All final and non-final office actions for U.S. Appl. No. 14/695,172 (P&G Case 13323).
PCT International Search Report and Written Opinion for PCT/US2014/054270 dated Nov. 20, 2014.
PCT International Search Report and Written Opinion for PCT/US2015/027410 dated Jul. 15, 2015.

* cited by examiner

*Primary Examiner* — Brian J Davis
(74) *Attorney, Agent, or Firm* — Linda M. Sivik

(57) ABSTRACT

The present invention is directed to a scalp care composition comprising from about 1% to about 99% of a volatile carrier wherein less than about 10% is a volatile solvent; from about 0.05% to about 10% of a polymeric rheology modifier and mixtures thereof; from about 0.03% to about 1% of particulate scalp benefit agent; from about 0.1% to about 5% of a solubilizing agent wherein the composition is shear thinning and has a zero shear viscosity value measured at 0.01 Pa of greater than about 1,500 Pa s.

17 Claims, 3 Drawing Sheets

SCALP CARE COMPOSITION WITH WELL DISPERSED PARTICULATE SCALP BENEFIT AGENTS

FIELD OF THE INVENTION

The present invention relates to a scalp care composition comprising one or more actives useful for treating dandruff.

BACKGROUND OF THE INVENTION

Hair and scalp leave on treatment compositions comprising various combinations of hair and scalp actives, are known in the art and are commercially available. These compositions may have rheological properties that optimize the consumer perceived usage experience (non-dripping, spread, coverage, etc.).

Anti-dandruff hair rinse off products are also commercially available. Anti-dandruff shampoos, conditioners, and other rinse off treatments typically incorporate an anti-dandruff active. One type of anti-dandruff agents are particulate, crystalline anti-dandruff agents, such as sulfur, selenium disulfide and multi-valent metal salts of pyridinethione. Soluble anti-dandruff agents, such as ketoconazole, are also available.

Nevertheless, some consumers desire an anti-dandruff leave on treatment which provides a level of anti-dandruff efficacy that can replace other anti-dandruff rinse off products or is used in addition to rinse off anti-dandruff products or provide leave on benefits to hair and scalp that are difficult to achieve with a rinse off product. Consequently, a need exists for a treatment product that combines core anti-dandruff efficacy with additional scalp health and hair benefits that the consumer can notice and feel, i.e. effective, and is delightful to use.

The present invention involves a scalp-directed leave-on treatment with particulate active ingredient (ZPT) that is well dispersed without the use of high levels of volatile organic solvents. The exclusion of volatile organic solvents (e.g. ethanol) can typically cause agglomeration of the particulate active, via an interaction with insoluble hydrophobic components of the composition (e.g. perfume). This agglomeration can lead to a reduction in the efficacy of the product, as well as potential product stability issues. The use of low levels of certain solubilizing agents can mitigate this agglomeration.

SUMMARY OF THE INVENTION

The present invention is directed to a scalp care composition comprising from about 1% to about 99% of a volatile carrier wherein less than about 10% is a volatile solvent; from about 0.05% to about 10% of a polymeric rheology modifier and mixtures thereof; from about 0.03% to about 1% of particulate scalp benefit agent from about 0.1% to about 5% of a solubilizing agent; wherein the composition is shear thinning and has a zero shear viscosity value measured at 0.01 Pa of greater than about 1,500 Pa s.

These and other features, aspects, and advantages of the present invention will become evident to those skilled in the art from a reading of the present disclosure.

DETAILED DESCRIPTION OF THE INVENTION

Figure 1:
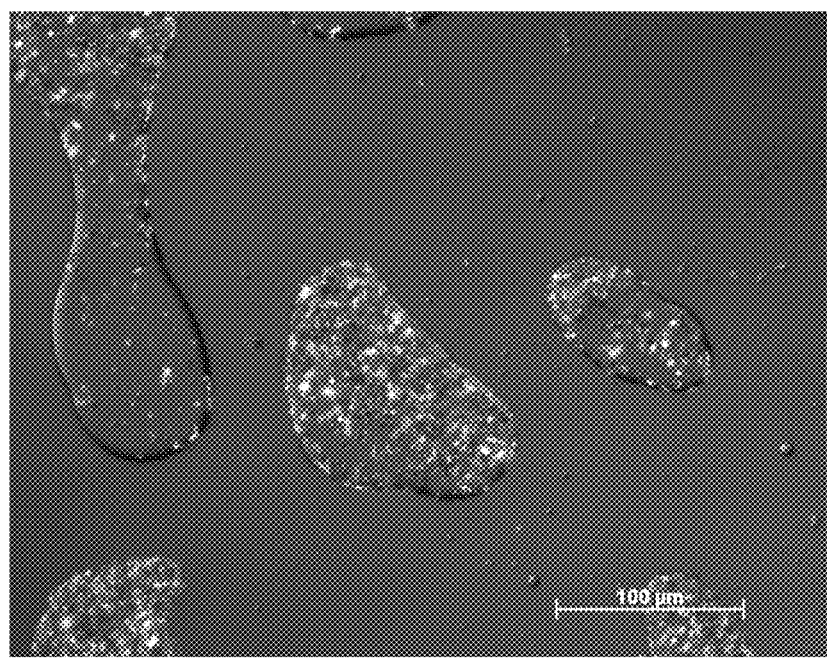
FIG. 1 is an image of microscopy demonstrating agglomerated particulate scalp benefit agent.

All percentages and ratios used herein are by weight of the total composition, unless otherwise designated. All measurements are understood to be made at ambient conditions, where "ambient conditions" means conditions at about 25° C., under about one atmosphere of pressure, and at about 50% relative humidity, unless otherwise designated. All numeric ranges are inclusive of narrower ranges; delineated upper and lower range limits are combinable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

"Apply" or "application," as used in reference to a composition, means to apply or spread the compositions of the present invention onto keratinous tissue such as the hair.

"Dermatologically acceptable" or "cosmetically acceptable" means that the compositions or components described are suitable for use in contact with human skin tissue without undue toxicity, incompatibility, instability, allergic response, and the like. All compositions described herein which have the purpose of being directly applied to keratinous tissue are limited to those being cosmetically acceptable.

"Safe and effective amount" means an amount of a compound or composition sufficient to significantly induce a positive benefit.

"Leave-on," in reference to compositions, means compositions intended to be applied to and allowed to remain on the keratinous tissue. These leave-on compositions are to be distinguished from compositions, which are applied to the hair and subsequently (within a few minutes or less) removed either by washing, rinsing, wiping, or the like. Leave-on compositions exclude rinse-off applications such as shampoos, rinse-off conditioners, facial cleansers, hand cleansers, body washes, or body cleansers. The leave-on compositions may be substantially free of cleansing or detersive surfactants. For example, "leave-on compositions" may be left on the keratinous tissue for at least 15 minutes. For example, leave-on compositions may comprise less than 1% detersive surfactants, less than 0.5% detersive surfactants, or 0% detersive surfactants. The compositions may, however, contain emulsifying, dispersing or other processing surfactants that are not intended to provide any significant cleansing benefits when applied topically to the hair.

"Soluble" means at least about 0.1 g of solute dissolves in 100 ml of solvent, at 25° C. and 1 atm of pressure.

All ratios are weight ratios, unless specifically stated otherwise. All ranges are inclusive and combinable. The number of significant digits conveys neither a limitation on the indicated amounts nor on the accuracy of the measurements. The term "molecular weight" or "M.Wt." as used herein refers to the weight average molecular weight unless otherwise stated. The weight average molecular weight may be measured by gel permeation chromatography "QS" means sufficient quantity for 100%.

The term "substantially free from" or "substantially free of" as used herein means less than about 1%, or less than about 0.8%, or less than about 0.5%, or less than about 0.3%, or about 0%, by total weight of the composition.

"Hair," as used herein, means mammalian hair including scalp hair, facial hair and body hair, particularly on hair on the human head and scalp.

"Derivatives," as used herein, includes but is not limited to, amide, ether, ester, amino, carboxyl, acetyl, acid, salt and/or alcohol derivatives of a given compound.

"Polymer," as used herein, means a chemical formed from the polymerisation of two or more monomers. The term "polymer" as used herein shall include all materials made by the polymerisation of monomers as well as natural polymers. Polymers made from only one type of monomer are called homopolymers. A polymer comprises at least two monomers. Polymers made from two or more different types of monomers are called copolymers. The distribution of the different monomers can be calculated statistically or blockwise, both possibilities are suitable for the present invention. Except if stated otherwise, the term "polymer" used herein includes any type of polymer including homopolymers and copolymers.

I. Scalp Care Compositions

Solubilizing Agents

The scalp care composition of the present invention may include one or more solubilizing agents. Nonlimiting examples of solubilizing agent can be water miscible nonionic surfactants, such as alkyl alkoxylate ethers, alkoxylated esters, organic acid esters or ethers of sugars or polysaccharides, glycol esters, glycerin esters and others. More specific classes that can serve as solubilizing agents are saturated or unsaturated alkyl ethoxylate ethers, ethoxylated organic acid esters (saturated or unsaturated), sorbate esters, polysorbates. Nonlimiting examples of specific materials that can serve as solubilizing agents include laureth-12, laureth-23, oleth-10, oleth-20, steareth-20, steareth-21, ceteth-20, PPG-26 Buteth-26, such as Creasoluble No. 4, PPG-1-PEG-9 lauryl glycol ether, PEG-40 hydrogenated castor oil, such as Cremaphor RH40, PEG-25 hydrogenated castor oil, yPEG-50 hydrogenated castor oil, POE-30 castor oil, POE-40 castor oil, heptyl glucoside, such as Sepiclear G7, Polysorbate-80, such as Tween 80, Polysorbate-20, Polysorbate-28, Polysorbate-60, Polysorbrate-61, Polysorbate-85, glyceryl stearate, PEG-20 stearate, PEG-40 stearate, PEG-100 stearate, PEG-8 dilaurate, sorbitan monooleate, sorbitan monolaurate, and others.

The scalp care composition may include from about 0.1% to about 5% of one or more solubilizing, agent, further from about 0.5% to about 3% of one or more solubilizing agents, and further from about 1% to about 2% of one or more solubilizing agents.

Solvents

The scalp care composition may include one or more solvents. The scalp care composition may include one or more organic solvents. Non-limiting examples may include dipropyleneglycol, propylene glycol, butylene glycol, 1,4-butanediol, 3-allyloxy-1,2-propanediol, dipropylene glycol n-butyl ether, 1,2-hexanediol, dimethyl isosorbide, ethanol, 1,3-butanediol, 1,3-propanediol, 2,2'-thiodiethanol, and 1,6-hexanediol, or combinations thereof.

The scalp care composition may further include one or more additional hair growth stimulating agents, such as those disclosed in U.S. Patent Application Publication No. 2010/0120871. Accordingly, non-limiting examples of additional hair growth stimulating agents include indole compounds, xanthine compounds, vitamin $B_3$ compounds, panthenol compounds, and derivatives thereof.

Indole Compounds

The scalp care compositions can further include an indole compound. As used herein, "indole compound" means one or more indoles, derivatives thereof, mixtures thereof, or salts thereof. Indole compounds that can be useful herein include, but are not limited to, indole-3-acetic acid and indole-3-carbinol. The indole compound may comprise an indole derivative at 3 and/or 5 position of the indole ring. The indole compound may comprise one or more of Indole-3-acetic acid (CAS#87-51-4), Indole-3-carbinol (CAS#700-06-1), 3-Methoxymethylindole (CAS#78440-76-3), 5-Methoxytryptophol (CAS#712-09-4), 5-Hydroxytryptophol (CAS#154-02-9), Tryptophol (CAS#526-55-6), 5-methoxy-1H-Indole-3-methanol (CAS#77419-78-4), 5-methyl-1H-Indole-3-methanol (CAS#215997-77-6), 5-fluoro-1H-Indole-3-methanol (CAS#773869-43-5), 5-Hydroxyindol-3-ylacetic acid (CAS#54-16-0), and 5-hydroxy-1H-Indole-3-propanoic acid (CAS#103986-23-8). Accordingly, the composition may include from about 0.1% to about 10% of the indole compound, from about 0.5% to about 5% of the indole compound, or from about 1% to about 2% of the indole compound, for example, wherein the percentage is a weight percentage based on the total weight of the final hair care composition.

Xanthine Compounds

The scalp care compositions can further include a xanthine compound. As used herein, "xanthine compound" means one or more xanthines, derivatives thereof, and mixtures thereof. Xanthine compounds that can be useful herein include, but are not limited to, caffeine, xanthine, 1-methylxanthine, theophylline, theobromine, derivatives thereof, and mixtures thereof. Accordingly, the composition may include from about 0.1% to about 10% of the xanthine compound, from about 0.5% to about 5% of the xanthine compound, or from about 1% to about 2% of the xanthine compound, for example, wherein the percentage is a weight percentage based on the total weight of the final hair care composition. For example, the hair care composition may further include about 0.75% of caffeine.

In the scalp care composition, the amount of xanthine may be decreased to lessen potential white residue the may result from various formulations when the xanthine is present in higher amounts. The scalp care composition may comprise from about 0.01% to about 1% xanthine, alternative from about 0.01% to about 0.75% xanthine, alternatively from about 0.01% to about 0.5% xanthine, alternatively from about 0.01% to about 0.25% xanthine, and alternatively from about 0.01% to about 0.1% xanthine. The scalp care composition may have no xanthine.

Vitamin $B_3$ Compounds

The scalp care compositions can further include a vitamin B3 compound. As used herein, "vitamin $B_3$ compound" means nicotinic acid, niacinamide, nicotinyl alcohol, derivatives thereof, and mixtures thereof. The vitamin $B_3$ compound may be included as the substantially pure material, or as an extract obtained by suitable physical and/or chemical isolation from natural (e.g., plant) sources. The scalp composition may include from about 0.1% to about 25% of the vitamin $B_3$ compound; from about 0.1% to about 15% of the vitamin $B_3$ compound; from about 0.1% to about 7.5%, from about 3.5% to about 7.5% of the vitamin $B_3$ compound, for example, wherein the percentage is a weight percentage based on the total weight of the final hair care composition. The scalp care composition may further include about 2.5% of vitamin $B_3$.

Panthenol Compounds

The scalp care compositions can further comprise a panthenol compound. As used herein, the term "panthenol compound" includes panthenol, one or more pantothenic acid derivatives, and mixtures thereof. Non-limiting examples of panthenol compounds include D-panthenol ([R]-2,4-dihydroxy-N-[3-hydroxypropyl)]-3,3-dimethylbutamide), D,L-panthenol, pantothenic acids and their salts (e.g., the calcium salt), panthenyl triacetate, royal jelly, panthetine, pantotheine, panthenyl ethyl ether, pangamic acid, pantoyl lactose, Vitamin B complex, or mixtures thereof. Accordingly, the scalp care composition may include from about 0.01% to about 5% of the panthenol compound, the scalp care composition may include from about 0.01% to 2.% of the panthenol compound, the scalp care composition may include from about 0.05% to about 2% of the panthenol compound; and the composition may include from about 0.1% to about 1% of the panthenol compound, for example, wherein the percentage is a weight percentage based on the total weight of the final hair care composition. The scalp care composition may further include about 0.15% of panthenol.

According to another aspect of the present invention, the scalp care compositions may be free of oleanolic acid and/or biotinyl-GHK, which is contrary to that described in U.S. Patent Application No. 20060067905.

Rheology Modifier

The scalp care composition may comprise a rheology modifier to improve various properties, such as increase the substantivity of the composition, improve the composition stability, non-dripping properties, sprayability and/or spreadability. Any suitable rheology modifier can be used. The scalp care composition may comprise from about 0.05% to about 10% of a rheology modifier, from about 0.1% to about 10% of a rheology modifier, from about 0.5% to about 2% of a rheology modifier, from about 0.7% to about 2% of a rheology modifier, from about 1% to about 1.5% of a rheology modifier. The rheology modifier may be a polyacrylamide thickener. The rheology modifier may be a polymeric rheology modifier.

The scalp care composition may comprise rheology modifiers that are homopolymers based on acrylic acid, methacrylic acid or other related derivatives, non-limiting examples include polyacrylate, polymethacrylate, polyethylacrylate, and polyacrylamide.

The rheology modifiers may be alkali swellable and hydrophobically-modified alkali swellable acrylic copolymers or methacrylate copolymers non-limiting examples include acrylic acid/acrylonitrogens copolymer, acrylates/steareth-20 itaconate copolymer, acrylates/ceteth-20 itaconate copolymer, acrylates/aminoacrylates copolymer, acrylates/steareth-20 methacrylate copolymer, acrylates/beheneth-25 methacrylate copolymer, acrylates/steareth-20 methacrylate crosspolymer, acrylates/vinylneodecanoate crosspolymer, and acrylates/C10-C30 alkyl acrylate crosspolymer.

The rheology modifiers may be crosslinked acrylic polymers, a non-limiting example includes carbomers.

The rheology modifiers may be alginic acid based materials. Non-limiting examples include sodium alginate, and alginic acid propylene glycol esters.

The rheology modifier may be an associative polymeric thickeners. Non-limiting examples include hydrophobically modified cellulose derivatives, hydrophobically modified alkoxylated urethane polymers. Specific materials may include PEG-150/decyl alcohol/SMDI copolymer, PEG-150/stearyl alcohol/SMDI copolymer, and polyurethane-39.

Other non-limiting examples include hydrophobically modified, alkali swellable emulsions, such as hydrophobically modified polypolyacrylates, hydrophobically modified polyacrylic acids, and hydrophobically modified polyacrylamides. Other non-limiting examples include hydrophobically modified polyethers wherein these materials may have a hydrophobe that can be selected from cetyl, stearyl, oleayl, and combinations thereof, and a hydrophilic portion of repeating ethylene oxide groups with repeat units from 10-300, from 30-200, or from 40-150. Specific materials of this class include PEG-120-methylglucose dioleate, PEG-(40 or 60) sorbitan tetraoleate, PEG-150 pentaerythrityl tetrastearate, PEG-55 propylene glycol oleate, and PEG-150 distearate.

The rheology modifier may be cellulose and derivatives. Nonlimiting examples include microcrystalline cellulose, carboxymethylcelluloses, hydroxyethylcellulose, hydroxypropylcellulose, hydroxypropylmethylcellulos, methylcellulose, ethyl cellulose, nitro cellulose, cellulose sulfate, cellulose powder, hydrophobically modified celluloses The rheology modifier may be a guar and guar derivatives. Non-limiting examples include hydroxypropyl guar, and hydroxypropyl guar hydroxypropyl trimonium chloride. The rheology modifier may be polyethylene oxide-polypropyne oxide copolymers. The rheology modifier may be polyvinylpyrrolidone, crosslinked polyvinylpyrrolidone and derivatives. The rheology modifier may be Polyvinyalcohol and derivatives. The rheology modifier may be polyethyleneimine and derivatives.

The rheology modifier may be silica. Non-limiting examples include fumed silica, precipitated silica, and silicone-surface treated silica.

The rheology modifier may be water-swellable clays. Non-limiting examples include laponite, bentolite, montmorilonite, smectite, and hectonite.

The rheology modifier may be gums. Non-limiting examples include xanthan gum, guar gum, hydroxypropyl guar gum, Arabia gum, tragacanth, galactan, carob gum, karaya gum, and locust bean gum.

The rheology modifier may be dibenzylidene sorbitol, karaggenan, pectin, agar, quince seed (Cydonia oblonga Mill), starch (from rice, corn, potato, wheat, etc), starch-derivatives (e.g. carboxymethyl starch, methylhydroxypropyl starch), algae extracts, dextran, succinoglucan, and pulleran, Non-limiting examples of rheology modifiers include acrylamide/ammonium acrylate copolymer (and)polyisobutene (and) polysorbate 20, acrylamide/sodium acryloyldimethyl taurate copolymer/isohexadecane/polysorbate 80, acrylates copolymer; acrylates/beheneth-25 methacrylate copolymer, acrylates/C10-C30 alkyl acrylate crosspolymer, acrylates/steareth-20 itaconate copolymer, ammonium polyacrylate/Isohexadecane/PEG-40 castor oil, C12-16 alkyl PEG-2 hydroxypropylhydroxyethyl ethylcellulose (HM-EHEC), carbomer, crosslinked polyvinylpyrrolidone (PVP), dibenzylidene sorbitol, hydroxyethyl ethylcellulose (EHEC), hydroxypropyl methylcellulose (HPMC), hydroxypropyl methylcellulose (HPMC), hydroxypropylcellulose (HPC), methylcellulose (MC), methylhydroxyethyl cellulose (MEHEC), PEG-150/decyl alcohol/SMDI copolymer, PEG-150/stearyl alcohol/SMDI copolymer, polyacrylamide/C13-14 isoparaffin/laureth-7, polyacrylate 13/polyisobutene/polysorbate 20, polyacrylate crosspolymer-6, polyamide-3, polyquaternium-37 (and) hydrogenated polydecene (and) trideceth-6, polyurethane-39, sodium acrylate/acryloyldimethyltaurate/dimethylacrylamide, crosspolymer (and) isohexadecane (and) polysorbate 60, and sodium polyacrylate. Exemplary commercially-available rheology modifiers include ACULYN™ 28, Klucel M CS, Klucel H CS, Klucel G CS, SYLVACLEAR AF1900V, SYLVACLEAR PA1200V, Benecel E10M, Benecel K35M, Optasense RMC70, ACULYN™33, ACULYN™46, ACULYN™22, ACULYN™44, Carbopol Ultrez 20, Carbopol Ultrez 21, Carbopol Ultrez 10, Carbopol Ulterez 30, Carbopol 1342, Sepigel™ 305, Simulgel™600, Sepimax Zen, and combinations thereof.

Carrier

According to another aspect of the present invention, the scalp care compositions may further include at least about 20 weight percent of an aqueous carrier. The aqueous carrier may be prepared from demineralized or distilled water, for example. The aqueous carrier comprises water or a combination of water with organic solvents (miscible or non-miscible with water) or silicone solvents. A volatile carrier may include water or a mixture of water and organic solvents. The solvents may be dermatologically acceptable. The carrier may comprise water with minimal or no significant concentrations of organic solvent, except as otherwise incidentally incorporated into the composition as minor ingredients of other components. Water, organic and silicone solvents that have boiling points below or equal to 250° C. are volatile solvents and volatile carriers. Volatile Solvents may have a boing point below or equal to 90° C., non-limiting examples include ethanol. Solvents with boiling points above 250° C. are considered non-volatile. In the present invention, the composition may have from about 1% to about 99% of a volatile carrier wherein less than about 10% is a volatile solvent.

Non-limiting examples of a carrier may include water and water solutions of lower alkyl alcohols and polyhydric alcohol, the lower alkyl alcohols such as monohydric alcohols having 1 to 6 carbons, in one aspect, ethanol and isopropanol, and polyhydric alcohols such as glycols, glycerin and other diols.

Other acceptable carriers that may be used in the aqueous carrier include, but are not limited to alcohol compounds, such as ethanol. The composition may comprise alcohol, dipropylene glycol, and/or water.

The scalp care compositions may have a pH ranging from about 3.0 to about 10, which may be measured by taking a direct pH measurement using a standard hydrogen electrode of the composition at 25° C. Accordingly, the pH of the hair care composition may be within the range from about 4 to about 9, as a non-limiting example.

Scalp Benefit Agent

The composition may comprise a scalp benefit agent, a non-limiting example being an anti-dandruff active, which may be an anti-dandruff active particulate. The anti-dandruff active is selected from the group consisting of pyridinethione salts, zinc carbonate, azoles, such as ketoconazole, econazole, and elubiol, selenium sulphide, particulate sulfur, keratolytic agents such as salicylic acid, and mixtures thereof. The anti-dandruff particulate may be a pyridinethione salt. Such anti-dandruff particulate should be physically and chemically compatible with the components of the composition, and should not otherwise unduly impair product stability, aesthetics or performance.

Pyridinethione particulates are suitable particulate anti-dandruff actives for use in composition of the present invention. The anti-dandruff active may be a 1-hydroxy-2-pyridinethione salt and is in particulate form. The concentration of pyridinethione anti-dandruff particulate may range from about 0.01% to about 5%, by weight of the composition, or from about 0.1% to about 3%, or from about 0.1% to about 2%. The pyridinethione salts are those formed from multi-valent metals such as zinc, tin, cadmium, magnesium, aluminium and zirconium, generally zinc, typically the zinc salt of 1-hydroxy-2-pyridinethione (known as "zinc pyridinethione" or "ZPT"; zinc pyrithione), commonly 1-hydroxy-2-pyridinethione salts in platelet particle form. The 1-hydroxy-2-pyridinethione salts in platelet particle form may have an average particle size of up to about 20 microns, or up to about 5 microns, or up to about 2.5 microns. Salts formed from other cations, such as sodium, may also be suitable. Pyridinethione anti-dandruff actives are described, for example, in U.S. Pat. Nos. 2,809,971; 3,236,733; 3,753,196; 3,761,418; 4,345,080; 4,323,683; 4,379,753; and 4,470,982.

In addition to the anti-dandruff active selected from polyvalent metal salts of pyrithione, the composition may further comprise one or more anti-fungal and/or anti-microbial actives. The anti-microbial active is selected from the group consisting of coal tar, sulfur, charcoal, whitfield's ointment, castellani's paint, aluminium chloride, gentian violet, octopirox (piroctone olamine), ciclopirox olamine, undecylenic acid and its metal salts, potassium permanganate, selenium sulphide, sodium thiosulfate, propylene glycol, oil of bitter orange, urea preparations, griseofulvin, 8-hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone, and azoles, and mixtures thereof. The anti-microbial may be selected from the group consisting of: itraconazole, ketoconazole, selenium sulphide, coal tar, and mixtures thereof.

The azole anti-microbials may be an imidazole selected from the group consisting of: benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and mixtures thereof, or the azole anti-microbials is a triazole selected from the group consisting of: terconazole, itraconazole, and mixtures thereof. When present in the composition, the azole anti-microbial active is included in an amount of from about 0.01% to about 5%, or from about 0.1% to about 3%, or from about 0.3% to about 2%, by total weight of the composition. The azole anti-microbial active may be ketoconazole. The sole anti-microbial active may be ketoconazole.

The present invention may also comprise a combination of anti-microbial actives. The combination of anti-microbial active is selected from the group of combinations consisting of: octopirox and zinc pyrithione, pine tar and sulfur, salicylic acid and zinc pyrithione, salicylic acid and elubiol, zinc pyrithione and elubiol, zinc pyrithione and climbazole, octopirox and climbazole, salicylic acid and octopirox, and mixtures thereof.

The composition comprises an effective amount of a zinc-containing layered material. The scalp care composition may comprise from about 0.001% to about 10%, or from about 0.01% to about 7%, or from about 0.1% to about 5%, from about 0.2% to about 5% of a zinc-containing layered material, by total weight of the composition.

Zinc-containing layered materials may be those with crystal growth primarily occurring in two dimensions. It is conventional to describe layer structures as not only those in which all the atoms are incorporated in well-defined layers, but also those in which there are ions or molecules between the layers, called gallery ions (A. F. Wells "Structural Inorganic Chemistry" Clarendon Press, 1975). Zinc-containing layered materials (ZLMs) may have zinc incorporated in the layers and/or be components of the gallery ions. The following classes of ZLMs represent relatively common examples of the general category and are not intended to be limiting as to the broader scope of materials which fit this definition.

Many ZLMs occur naturally as minerals. The ZLM may be selected from the group consisting of: hydrozincite (zinc carbonate hydroxide), basic zinc carbonate, aurichalcite (zinc copper carbonate hydroxide), rosasite (copper zinc carbonate hydroxide), and mixtures thereof. Related minerals that are zinc-containing may also be included in the composition. Natural ZLMs can also occur wherein anionic layer species such as clay-type minerals (e.g., phyllosilicates) contain ion-exchanged zinc gallery ions. All of these natural materials can also be obtained synthetically or formed in situ in a composition or during a production process.

Another common class of ZLMs, which are often, but not always, synthetic, is layered double hydroxides. The ZLM may be a layered double hydroxide conforming to the formula $[M^{2+}_{1-x}M^{3+}_{x}(OH)_2]^{x+}A^{m-}_{x/m}\cdot nH_2O$ wherein some or all of the divalent ions ($M^{2+}$) are zinc ions (Crepaldi, E L, Pava, P C, Tronto, J, Valim, J B *J. Colloid Interfac. Sci.* 2002, 248, 429-42).

Yet another class of ZLMs can be prepared called hydroxy double salts (Morioka, H., Tagaya, H., Karasu, M, Kadokawa, J, Chiba, K *Inorg. Chem.* 1999, 38, 4211-6). The ZLM may be a hydroxy double salt conforming to the formula $[M^{2+}_{1-x}M^{2+}_{1+x}(OH)_{3(1-y)}]^{+}A^{n-}_{(1=3y)/n}\cdot nH_2O$ where the two metal ions ($M^{2+}$) may be the same or different. If they are the same and represented by zinc, the formula simplifies to $[Zn_{1+x}(OH)_2]^{2x+}2xA^{-}\cdot nH_2O$. This latter formula represents (where x=0.4) materials such as zinc hydroxychloride and zinc hydroxynitrate. The ZLM may be zinc hydroxychloride and/or zinc hydroxynitrate. These are related to hydrozincite as well wherein a divalent anion replace the monovalent anion. These materials can also be formed in situ in a composition or in or during a production process.

The composition may comprise basic zinc carbonate. Commercially available sources of basic zinc carbonate include Zinc Carbonate Basic (Cater Chemicals: Bensenville, Ill., USA), Zinc Carbonate (Shepherd Chemicals: Norwood, Ohio, USA), Zinc Carbonate (CPS Union Corp.: New York, N.Y., USA), Zinc Carbonate (Elementis Pigments: Durham, UK), and Zinc Carbonate AC (Bruggemann Chemical: Newtown Square, Pa., USA). Basic zinc carbonate, which also may be referred to commercially as "Zinc Carbonate" or "Zinc Carbonate Basic" or "Zinc Hydroxy Carbonate", is a synthetic version consisting of materials similar to naturally occurring hydrozincite. The idealized stoichiometry is represented by $Zn_5(OH)_6(CO_3)_2$ but the actual stoichiometric ratios can vary slightly and other impurities may be incorporated in the crystal lattice.

In scalp care compositions having a zinc-containing layered material and a pyrithione or polyvalent metal salt of pyrithione, the ratio of zinc-containing layered material to pyrithione or a polyvalent metal salt of pyrithione is from about 5:100 to about 10:1, or from about 2:10 to about 5:1, or from about 1:2 to about 3:1.

Polyols

Polyols are a component of the present invention, with a nonlimiting example of a polyol being glycerin. Glycerin is a colorless, odorless, viscous liquid that is very common for use in personal care applications and pharmaceutical formulations. Glycerin contains three hydroxyl groups that are responsible for its solubility in water and its humectant nature. Glycerin is well known as hair and skin benefit agent in personal care applications. This material can penetrate into a human hair to provide conditioning and softness via plasticization of the hair fiber while maintaining a very clean surface feel. Glycerin has been observed to clean more hydrophobic soil components (i.e. sebum) than water.

The levels of glycerin range from about 0.1% to about 10%, from about 0.5% to about 8%, from about 1% to about 7% and from about 3.0% to about 6.0% by weight of the shampoo composition.

In the scalp care composition, other polyols may be used. Non-limiting examples include propylene glycol, sugar polyols such as sorbitol, aloe vera gel and honey.

Silicones

The conditioning agent of the compositions of the present invention can be a silicone conditioning agent. The silicone conditioning agent may comprise volatile silicone, non-volatile silicone, or combinations thereof. The concentration of the silicone conditioning agent typically ranges from about 0.01% to about 10%, by weight of the composition, from about 0.1% to about 8%, from about 0.1% to about 5%, and/or from about 0.2% to about 3%. Non-limiting examples of suitable silicone conditioning agents, and optional suspending agents for the silicone, are described in U.S. Reissue Pat. No. 34,584, U.S. Pat. Nos. 5,104,646, and 5,106,609, which descriptions are incorporated herein by reference. The silicone conditioning agents for use in the compositions of the present invention can have a viscosity, as measured at 25° C., from about 20 to about 2,000,000 centistokes ("cSt"), from about 1,000 to about 1,800,000 cSt, from about 50,000 to about 1,500,000 cSt, and/or from about 100,000 to about 1,500,000 cSt.

The dispersed silicone conditioning agent particles typically have a volume average particle diameter ranging from about 0.01 micrometers to about 50 micrometers. For small particle application to hair, the volume average particle diameters typically range from about 0.01 micrometer to about 4 micrometers, from about 0.01 micrometers to about 2 micrometers, from about 0.01 micrometer to about 0.5 micrometers. For larger particle application to hair, the volume average particle diameters typically range from about 5 micrometers to about 125 micrometers, from about 10 micrometers to about 90 micrometers, from about 15 micrometers to about 70 micrometers, and/or from about 20 micrometers to about 50 micrometers.

Additional material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989), incorporated herein by reference.

Silicone emulsions suitable for use in the present invention and may include, but are not limited to, emulsions of insoluble polysiloxanes prepared in accordance with the descriptions provided in U.S. Pat. No. 4,476,282 and U.S. Patent Application Publication No. 2007/0276087. Accordingly, suitable insoluble polysiloxanes include polysiloxanes such as alpha, omega hydroxy-terminated polysiloxanes or alpha, omega alkoxy-terminated polysiloxanes having a molecular weight within the range from about 50,000 to about 500,000 g/mol. The insoluble polysiloxane can have an average molecular weight within the range from about 50,000 to about 500,000 g/mol. For example, the insoluble polysiloxane may have an average molecular weight within the range from about 60,000 to about 400,000; from about 75,000 to about 300,000; from about 100,000 to about 200,000; or the average molecular weight may be about 150,000 g/mol. The insoluble polysiloxane can have an average particle size within the range from about 30 nm to about 10 micrometers. The average particle size may be within the range from about 40 nm to about 5 micrometers, from about 50 nm to about 1 micrometers, from about 75 nm to about 500 nm, or about 100 nm, for example.

The average molecular weight of the insoluble polysiloxane, the viscosity of the silicone emulsion, and the size of the particle comprising the insoluble polysiloxane are determined by methods commonly used by those skilled in the art, such as the methods disclosed in Smith, A. L. *The Analytical Chemistry of Silicones*, John Wiley & Sons, Inc.: New York, 1991. For example, the viscosity of the silicone emulsion can be measured at 30° C. with a Brookfield viscosimeter with spindle 6 at 2.5 rpm. The silicone emulsion may further include an additional emulsifier together with the anionic surfactant, Other classes of silicones suitable for use in compositions of the present invention include but are not limited to: i) silicone fluids, including but not limited to, silicone oils, which are flowable materials having viscosity less than about 1,000,000 cSt as measured at 25° C.; ii) aminosilicones, which contain at least one primary, secondary or tertiary amine; iii) cationic silicones, which contain at least one quaternary ammonium functional group; iv) silicone gums; which include materials having viscosity greater or equal to 1,000,000 cSt as measured at 25° C.; v) silicone resins, which include highly cross-linked polymeric siloxane systems; vi) high refractive index silicones, having refractive index of at least 1.46, and vii) mixtures thereof.

Organic Conditioning Materials

The conditioning agent of the shampoo compositions of the present invention may also comprise at least one organic conditioning material such as oil or wax, either alone or in combination with other conditioning agents, such as the silicones described above. The organic material can be non-polymeric, oligomeric or polymeric. It may be in the form of oil or wax and may be added in the formulation neat or in a pre-emulsified form. Some non-limiting examples of organic conditioning materials include, but are not limited to: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-200, PEG-400, PEG-600, PEG-1000, PEG-2M, PEG-7M, PEG-14M, PEG-45M and mixtures thereof.

Scalp Health Actives

In the scalp care composition, a scalp health active may be added to provide scalp benefits in addition to the the anti-fungal/anti-dandruff efficacy provided by the ZPT. This group of materials is varied and provides a wide range of benefits including moisturization, barrier improvement, anti-fungal, and anti-oxidant, anti-itch, and sensates. Such skin health actives include but are not limited to: vitamin E and F, salicylic acid, glycols, glycolic acid, PCA, PEGs, erythritol, glycerin, lactates, hyaluronates, allantoin and other ureas, betaines, sorbitol, glutamates, xylitols, menthol, menthyl lactate, iso cyclomone, benzyl alcohol, and natural extracts/oils including peppermint, spearmint, argan, jojoba and aloe.

Optional Ingredients

The compositions of the present invention can also additionally comprise any suitable optional ingredients as desired. For example, the composition can optionally include other active or inactive ingredients.

The compositions may include other common hair ingredients such as minoxidil, silicones, glycerin, conditioning agents, and other suitable materials. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of nonlimiting materials that can be added to the composition herein. Examples of these ingredient classes include, but are not limited to: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, rheology modifiers, hair conditioning agents, and surfactants.

The formulations of the present invention may be present in typical hair care compositions. They may be in the form of solutions, dispersion, emulsions, powders, talcs, encapsulated, spheres, spongers, solid dosage forms, foams, and other delivery mechanisms. The composition of the present invention may be hair tonics, leave-on hair products such as conditioners, treatment, and styling products, rinse-off hair products such as conditioners, shampoos, and treatment products; and any other form that may be applied to the hair and preferably applied to the scalp.

II. METHODS

Particle Size Distribution Method (PSD)

Particle size distribution is determined using laser diffraction through the sample, specifically with a Horiba LA-950 equipped with a paste cell. The use of the paste cell is beneficial, as most particle analyzers use flow cells which require sample dilution for flowability, as well as >90% transparency at the longer optical path lengths. However, dilution would be unacceptable when characterizing agglomerates of particles as they could be broken up into primary particles by the dilution. The paste cell, with adjustable optical path length, allows for opaque samples to be imaged by significantly shortening the optical path length and characterizing in a static state.

Viscosity Test Method

Method which Provides a Zero Shear Viscosity Value

A zero shear viscosity as related to sedimentation and stability can be measured using the following method:

The viscosity of the scalp care composition may be determined by a cone and plate viscometer/rheometer which measures the viscous drag resulting from the sample material contained in the gap between a rotating cone and a stationary plate. The geometry of the cone and plate may be such that the entire sample is subjected to a uniform shear rate. To determine the relevant viscosity for stability and sedimentation an Advanced Rheometer 2000 fitted with a 4 degree, 6 centimeter Acrylic cone at 25° C. temperature using a 3.95 mL sample size and a solvent trap may be used with a procedure consists of a 2 minute relaxation time, followed by a constant stress creep step at 0.01 Pa. Using Stokes law, it can be calculated that the stress from gravity (sedimentation) on a particle with a radius of 2 micrometers and density 1800 kg/m³ in a fluid of density 920 kg/m³ can be approximated as 0.01 Pa. Shear rate is then determined by fitting a straight line through the strain versus time data collected from 60 seconds through 240 seconds using the Rheology Advantage Data Analysis package and viscosity at the specified stress is then calculated by stress/rate in Pa s. The composition may have a zero shear viscosity measured at 0.01 Pa of greater than about 1,500 Pa s, a zero shear viscosity measured at 0.01 Pa of greater than about 2,000 Pa s, or a zero shear viscosity measured at 0.01 Pa of greater than about 10,000 Pa s. Such viscosity allows for spreadability or sprayability of the present invention composition.

Results

Figure 2:
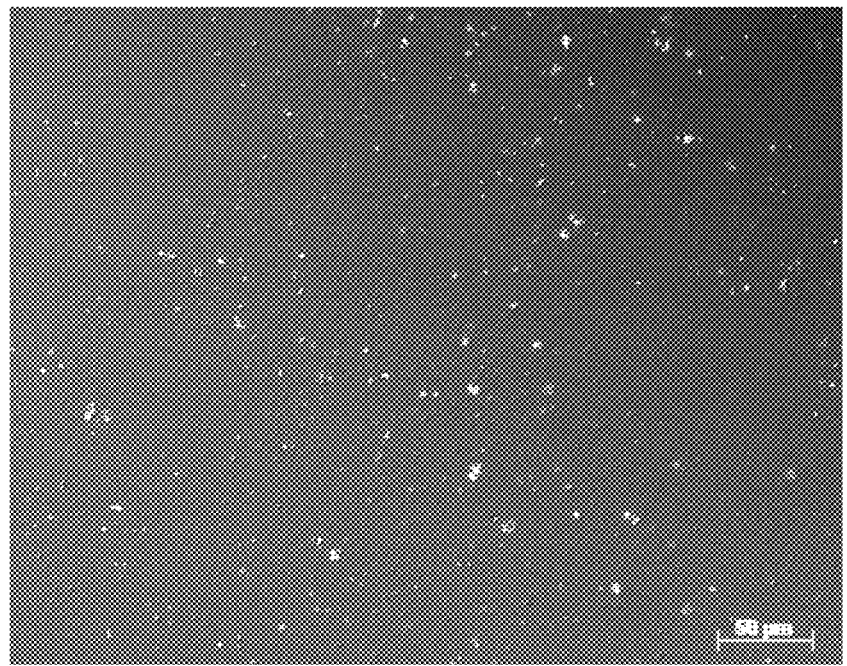
FIG. 2 is an image of microscopy demonstrating a well dispersed particulate scalp benefit agent.
Figure 3:
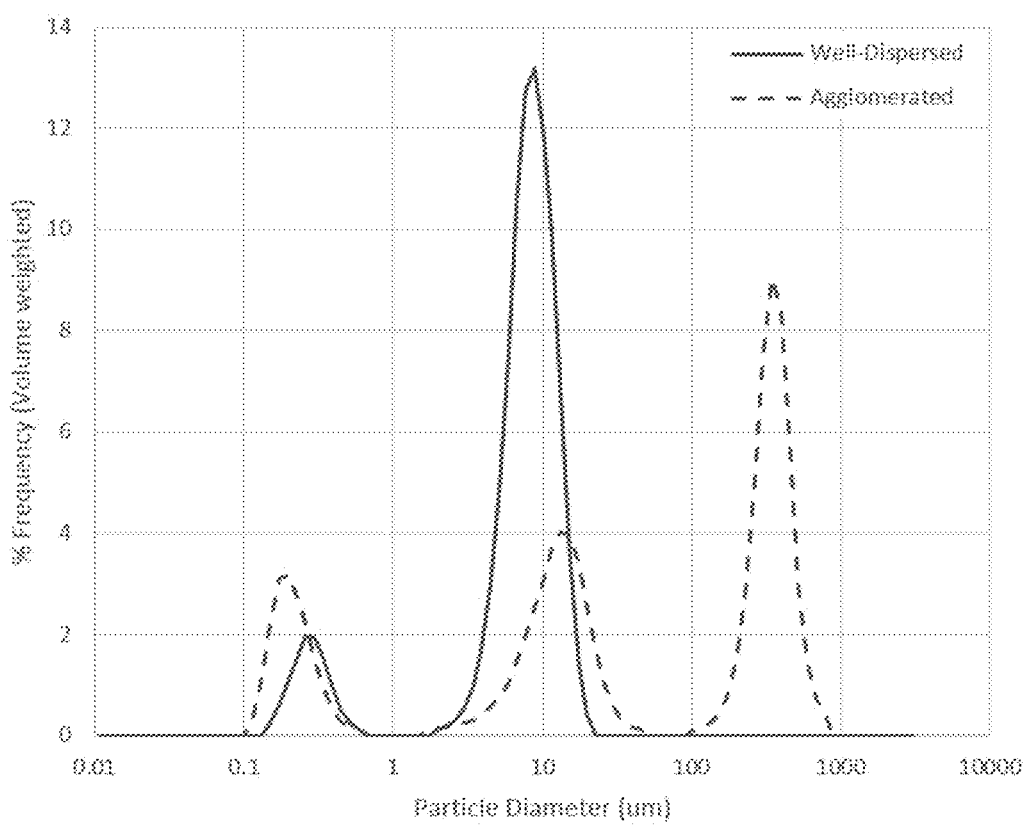
FIG. 3 is a Horiba paste cell particle size distribution of a particulate scalp benefit agent zinc pyrithione.

FIG. 1 is an image using standard light microscopy demonstrating agglomerated particulate scalp benefit agent from Example 2. FIG. 2 is an image using standard light microscopy demonstrating a well dispersed particulate scalp benefit agent from Example 9. FIG. 3 demonstrates that for a well dispersed particulate scalp benefit agent, such as Example 9, the particle size distribution is less than 100 µm as compared to the agglomerated sample, such as Example 2, which demonstrates a larger particle size distribution. These larger, agglomerated particles have significantly higher tendency to settle in a liquid carrier than smaller sized particles. Additionally, the agglomeration of a scalp benefit agent has been shown to reduce the anti-fungal efficacy of that treatment.

FORMULATIONS AND EXAMPLES

In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minors will vary depending on the physical and chemical characteristics of the particular ingredients selected to make the hair care composition.

| | Examples that agglomerate | | | | |
|---|---|---|---|---|---|
| Ingredient | Ex. 1 | Ex. 2 | Ex. 3 | Ex. 4 | Ex. 5 |
| Water | QS | QS | QS | QS | QS |
| Ethanol | — | 50 | 50 | — | — |
| Acrylates/C10-30 alkyl acrylate crosspolymer[1] | 0.17 | 0.35 | 0.35 | 0.17 | 0.17 |
| Zinc Pyrithione[2] | 0.1 | 0.1 | 0.1 | 0.1 | 0.1 |
| Panthenol | 0.15 | 0.15 | 0.15 | — | — |
| Niacinamide | 2.5 | 2.5 | 2.5 | — | — |
| Caffeine | 0.75 | 0.75 | 0.75 | — | — |
| Glycerin | 0.5 | 2 | 0.5 | — | — |
| Benzyl Alcohol | — | — | — | — | — |
| Phenoxyethanol, Ethylhexylglycerin Mixture[3] | — | — | — | — | — |
| PEG-40 Hydrogenated Castor Oil[4] | — | — | 0.25 | — | — |
| Heptyl Glucoside[5] | — | — | — | — | — |
| PPG-26-Buteth-26 | — | — | — | — | — |
| Polysorbate 80 | — | — | — | — | — |
| Laureth-23 | — | — | — | — | 1 |
| Bis-PEG/PPG-16/16 PEG/PPG 16/16 Dimethicone, Caprylic/Capric Triglyceride | 0.7 | 0.7 | 0.7 | 0.7 | 0.7 |
| Menthol | — | — | — | — | — |
| Perfume | 0.4 | 0.4 | 0.4 | 0.4 | 0.2 |
| Vitamin E Acetate | — | 0.4 | 0.75 | — | — |
| Tetrahydroxypropyl Ethylenediamin[6] | for adjusting the pH to about 5-7 | | | | |

| | Examples that don't agglomerate | | | | |
|---|---|---|---|---|---|
| Ingredient | Ex. 6 | Ex.7 | Ex. 8 | Ex. 9 | Ex. 10 |
| Water | QS | QS | QS | QS | QS |
| Ethanol | — | — | — | — | — |
| Acrylates/C10-30 alkyl acrylate crosspolymer[1] | 0.17 | 0.17 | 0.17 | 0.17 | 0.17 |
| Zinc Pyrithione[2] | 0.1 | 0.1 | 0.1 | 0.1 | 0.1 |
| Panthenol | 0.15 | 0.15 | 0.15 | — | — |
| Niacinamide | 2.5 | 2.5 | 2.5 | — | — |
| Caffeine | 0.75 | 0.75 | 0.75 | — | — |
| Glycerin | 0.5 | 0.5 | 0.5 | — | — |
| Benzyl Alcohol | 0.4 | 0.4 | 0.4 | — | — |
| Phenoxyethanol, Ethylhexylglycerin Mixture[3] | 1 | 1 | 1 | — | — |
| PEG-40 Hydrogenated Castor Oil[4] | 1 | 2 | — | — | — |
| Heptyl Glucoside[5] | — | — | 1.5 | — | — |
| PPG-26-Buteth-26 | — | — | — | 0.2 | — |
| Polysorbate 80 | — | — | — | — | 1 |
| Laureth-23 | — | — | — | — | — |
| Bis-PEG/PPG-16/16 PEG/PPG 16/16 Dimethicone, Caprylic/Capric Triglyceride | 0.7 | 0.7 | 0.7 | 0.7 | 0.7 |
| Menthol | — | 0.3 | — | — | — |
| Perfume | 0.4 | 0.4 | 0.4 | 0.2 | 0.2 |

| | | | | | |
|---|---|---|---|---|---|
| Vitamin E Acetate | — | — | — | — | — |
| Tetrahydroxypropyl Ethylenediamine[6] | | for adjusting the pH to about 5-7 | | | |

[1]as in Carbopol Ultrez 21 available from Lubrizol
[2]as in ZPT from Lonza Personal Care
[3]Phenoxyethanol, Ethylhexylglycerin Mixture is Euxyl ® PE9014
[4]as in Cremaphor RH40
[5]as in Sepiclear G7
[6]as in Neutrol Te from BASF Additional Examples/Combinations A. A scalp care composition comprising:
 a) from about 1% to about 99% of a volatile carrier wherein less than about 10% is a volatile solvent;
 b) from about 0.05% to about 10% of a polymeric rheology modifier and mixtures thereof;
 c) from about 0.03% to about 1% of particulate scalp benefit agent
 d) from about 0.1% to about 5% of a solubilizing agent;
 wherein the composition is shear thinning and has a zero shear viscosity value measured at 0.01 Pa of greater than about 1,500 Pa s.
B. A scalp care composition according to Paragraph A, wherein the solubilizing agent is alkyl alkoxylate ethers, alkoxylated esters, organic acid esters or ethers of sugars or polysaccharides, glycol esters, glycerin esters and mixtures thereof.
C. A scalp care composition according to Paragraph A-B, wherein the solubilizing agent is saturated or unsaturated alkyl ethoxylate ethers, ethoxylated organic acid esters (saturated or unsaturated), sorbate esters, polysorbates and mixtures thereof.
D. A scalp care composition according to Paragraph A-C, wherein the solubilizing agent is laureth-12, laureth-23, oleth-10, oleth-20, steareth-20, steareth-21, ceteth-20, PPG-26 Butteth-26, PPG-1-PEG-9 lauryl glocol ether, PEG-40 hydrogenated castor oil, PEG-25 hydrogenated castor oil, PEG-50 hydrogenated castor oil, POE-30 castor oil, POE-40 castor oil, heptyl glucoside, Polysorbate-80, Polysorbate-20, Polysorbate-28, Polysorbate-60, Polysorbate-61, Polysorbate-85, glyceryl stearate, PEG-20 stearate, PEG-40 stearate, PEG-100 stearate, PEG-8 dilaurate, sorbitan monooleate, sorbitan monolaurate, and mixtures thereof.
E. A scalp care composition according to Paragraph A-D, wherein the solubilizing agent is from about 0.5% to about 3%.
F. A scalp care composition according to Paragraph A-E, wherein the solubilizing agent is from about 1% to about 2%.
G. A scalp care composition according to Paragraph A-F, wherein the volatile carrier is water or a mixture of water and an organic solvent.
H. A scalp care composition according to Paragraph A-G, wherein the organic solvents are selected from the group consisting of dipropyleneglycol, propylene glycol, butylene glycol, 1,4-butanediol, 3-allyloxy-1,2-propanediol, dipropylene glycol n-butyl ether, 1,2-hexanediol, dimethyl isosorbide, ethanol, 1,3-butanediol, 1,3-propanediol, 2,2'-thiodiethanol, 1,6-hexanediol and combinations thereof.
I. A scalp care composition according to Paragraph A-H, wherein the polymeric rheology modifier is selected from the group consisting of homopolymers of acrylic acid, methacrylic acid or and derivatives, alkali swellable and hydrophobically-modified alkali swellable acrylic copolymers or methacrylate copolymers, crosslinked acrylic polymers, and an associative polymeric thickeners and mixtures thereof.
J. A scalp care composition according to Paragraph A-I, wherein the polymeric rheology modifier is an acrylates/C10-C30 alkyl acrylate crosspolymer.
K. A scalp care composition according to Paragraph A-J, wherein the polymeric rheology modifier is a crosslinked acrylic polymer.
L. A scalp care composition according to Paragraph A-K, wherein the particulate scalp benefit agent is selected from the group consisting metal pyridinethione salts, selenium sulfide, particulate sulfur, and mixtures thereof.
M. A scalp care composition according to Paragraph A-L, wherein particulate scalp benefit agent is zinc pyrithione.
N. A scalp care composition according to Paragraph A-M, wherein the composition further comprises glycerin.
O. A scalp care composition according to Paragraph A-N, wherein the composition further comprises niacinamide in the range of 0.1% to 7.5%.
P. A scalp care composition according to Paragraph A-O, wherein the composition further comprises caffeine in the range of 0.1% to 3.0%.
Q. A scalp care composition according to Paragraph A-P, wherein the composition further comprises panthenol in the range of 0.01% to 2.0%.
R. A scalp care composition according to Paragraph A-Q, wherein the composition further comprises a silicone.
S. A scalp care composition according to Paragraph A-R, wherein the composition is a leave-on composition.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While the present invention has been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A scalp care composition comprising:
    a) from about 1% to about 99% of a volatile carrier wherein less than about 10% is a volatile solvent;
    b) from about 0.05% to about 10% of a polymeric rheology modifier and mixtures thereof;
    c) from about 0.03% to about 1% of particulate scalp benefit agent wherein the particulate scalp benefit agent is zinc pyrithione;
    d) from about 0.1% to about 5% of a solubilizing agent; wherein the composition is shear thinning and has a zero shear viscosity value measured at 0.01 Pa of greater than about 1,500 Pa s.

2. A scalp care composition according to claim 1 wherein the solubilizing agent is alkyl alkoxylate ethers, alkoxylated esters, organic acid esters or ethers of sugars or polysaccharides, glycol esters, glycerin esters and mixtures thereof.

3. A scalp care composition according to claim 2 wherein the solubilizing agent is saturated or unsaturated alkyl ethoxylate ethers, ethoxylated organic acid esters (saturated or unsaturated), sorbate esters, polysorbates and mixtures thereof.

4. A scalp care composition according to claim 3 wherein the solubilizing agent is laureth-12, laureth-23, oleth-10, oleth-20, steareth-20, steareth-21, ceteth-20, PPG-26 Butteth-26, PPG-1-PEG-9 lauryl glocol ether, PEG-40 hydrogenated castor oil, PEG-25 hydrogenated castor oil, PEG-50 hydrogenated castor oil, POE-30 castor oil, POE-40 castor oil, heptyl glucoside, Polysorbate-80, Polysorbate-20, Polysorbate-28, Polysorbate-60, Polysorbate-61, Polysorbate-85, glyceryl stearate, PEG-20 stearate, PEG-40 stearate, PEG-100 stearate, PEG-8 dilaurate, sorbitan monooleate, sorbitan monolaurate, and mixtures thereof.

5. A scalp care composition according to claim 1 wherein the solubilizing agent is from about 0.5% to about 3%.

6. A scalp care composition according to claim 1 wherein the solubilizing agent is from about 1% to about 2%.

7. A scalp care composition according to claim 1 wherein the volatile carrier is water or a mixture of water and an organic solvent.

8. A scalp care composition according to claim 7 wherein the organic solvents are selected from the group consisting of dipropyleneglycol, propylene glycol, butylene glycol, 1,4-butanediol, 3-allyloxy-1,2-propanediol, dipropylene glycol n-butyl ether, 1,2-hexanediol, dimethyl isosorbide, ethanol, 1,3-butanediol, 1,3-propanediol, 2,2'-thiodiethanol, 1,6-hexanediol and combinations thereof.

9. A scalp care composition according to claim 1 wherein the polymeric rheology modifier is selected from the group consisting of homopolymers of acrylic acid, methacrylic acid or and derivatives, alkali swellable and hydrophobically-modified alkali swellable acrylic copolymers or methacrylate copolymers, crosslinked acrylic polymers, and an associative polymeric thickeners and mixtures thereof.

10. A scalp care composition according to claim 9 wherein the polymeric rheology modifier is an acrylates/C10-C30 alkyl acrylate crosspolymer.

11. A scalp care composition according to claim 9 wherein the polymeric rheology modifier is a crosslinked acrylic polymer.

12. A scalp care composition according to claim 1 wherein the composition further comprises glycerin.

13. A scalp care composition according to claim 1 wherein the composition further comprises niacinamide in the range of 0.1% to 7.5%.

14. A scalp care composition according to claim 1 wherein the composition further comprises caffeine in the range of 0.1% to 3.0%.

15. A scalp care composition according to claim 1 wherein the composition further comprises panthenol in the range of 0.01% to 2.0%.

16. A scalp care composition according to claim 1 wherein the composition further comprises a silicone.

17. A scalp care composition according to claim 1 wherein the composition is a leave-on composition.

* * * * *